United States Patent [19]
Cool et al.

[11] Patent Number: 5,895,429
[45] Date of Patent: *Apr. 20, 1999

[54] LEG PROSTHESIS WITH LOCKABLE KNEE JOINT

[75] Inventors: Jan Constant Cool, Pijnacker; Landoaldus Gerhardus Lemmers, Enschede, both of Netherlands

[73] Assignee: Ambroise Holland B.V., Enschede, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/737,048
[22] PCT Filed: May 4, 1995
[86] PCT No.: PCT/NL95/00162
    § 371 Date: Jan. 3, 1997
    § 102(e) Date: Jan. 3, 1997
[87] PCT Pub. No.: WO95/30391
    PCT Pub. Date: Nov. 16, 1995

[30] Foreign Application Priority Data

May 4, 1994 [NL] Netherlands ............... 9400733

[51] Int. Cl.$^6$ ............... A61F 2/60; A61F 2/64
[52] U.S. Cl. ............... 623/27; 623/35; 623/44
[58] Field of Search ............... 623/39–46, 27, 623/38, 50, 52, 35; 248/608, 609

[56] References Cited

U.S. PATENT DOCUMENTS

| 62,731 | 3/1867 | Carleton et al. ............... 623/41 |
| 2,170,580 | 8/1939 | Steele et al. ............... 623/41 |

(List continued on next page.)

FOREIGN PATENT DOCUMENTS

| 168889 | 9/1951 | Austria ............... 623/44 |
| 0141640 | 5/1985 | European Pat. Off. . |
| 2385385 | 10/1978 | France ............... 623/46 |
| 2470588 | 6/1981 | France . |
| 3227359 | 2/1983 | Germany . |
| 2013081 C1 | 5/1994 | Russian Federation ............... 623/39 |
| 1319845 A1 | 6/1987 | U.S.S.R. ............... 623/43 |
| 1351600 A1 | 11/1987 | U.S.S.R. ............... 623/43 |
| 132533 | 2/1921 | United Kingdom ............... 623/44 |
| 2 161 386 | 1/1986 | United Kingdom ............... 623/44 |
| 2 192 544 | 1/1988 | United Kingdom ............... 623/39 |

*Primary Examiner*—David H. Willse
*Attorney, Agent, or Firm*—Webb Ziesenheim Bruening Logsdon Orkin & Hanson, P.C.

[57] ABSTRACT

The invention relates to a prosthesis comprising first and second prosthesis parts connected for mutual movement which are characterized by a locking element for locking respectively releasing the prosthesis parts relative to each other. The parts are preferably connected for mutual movement by an artificial joint comprising a first and a second joint part. The locking element is spring biased and co-acts in a locked position with a recess in one of the joint parts, whereby tilting of the locking element is bounded, and which in the released position is substantially freely tiltable. The prosthesis can be further provided with a pin for actively placing the locking element out of the active reach of the recess. One of the two prosthesis parts connected for mutual movement is formed with a cup so that the prosthesis can be fixed to the remaining part of an amputated extremity. Opposite the cup are a brace, a perforated band, a tape and an eye which are utilized for fixing the prosthesis part to a higher located part of the remaining part of the amputated extremity. The other of the two prosthesis parts is formed by a device for replacing at least a part of the amputated extremity and is preferably provided with damping material.

15 Claims, 9 Drawing Sheets

U.S. PATENT DOCUMENTS

| | | | |
|---|---|---|---|
| 2,175,136 | 10/1939 | Stewart. | |
| 2,662,228 | 12/1953 | Bennington. | |
| 2,870,453 | 1/1959 | Vasquez | 623/43 |
| 3,309,715 | 3/1967 | Nader. | |
| 3,408,660 | 11/1968 | Walters. | |
| 3,453,663 | 7/1969 | Minor | 623/40 |
| 3,546,712 | 12/1970 | Tarte | 623/42 X |
| 4,038,705 | 8/1977 | Owens et al. | 623/38 X |
| 4,134,159 | 1/1979 | Wilson. | |
| 4,179,759 | 12/1979 | Smith | 623/41 |
| 4,756,712 | 7/1988 | Clover. | |
| 5,007,937 | 4/1991 | Fishman. | |
| 5,217,500 | 6/1993 | Phillips | 623/38 |
| 5,376,138 | 12/1994 | Bouchard et al. | 623/44 |
| 5,405,409 | 4/1995 | Knoth | 623/44 |
| 5,458,656 | 10/1995 | Phillips | 623/27 |

LEG PROSTHESIS WITH LOCKABLE KNEE JOINT

BACKGROUND OF THE INVENTION

The present invention relates to a prosthesis comprising two prosthesis parts connected for mutual movement.

FIELD OF THE INVENTION

A number of matters must be taken into account in the development of prostheses. A prosthesis must be comfortable, cosmetically acceptable and easily manageable. A prosthesis consists generally of two or more components. Firstly there is a component with which the prosthesis is attached to the remaining part of the amputated extremity, the stump, hereinafter referred to as the fixing part. Depending on the amputation, such a stump may be longer or shorter. In the case of exarticulations and amputations wherein a part of the upper leg or upper arm is also removed, an artificial joint is also required in addition to the fixing means. Each prosthesis further comprises a part which replaces the amputated extremity, further referred to as replacement part. In addition to simply replacing the amputated extremity, the replacement part has a number of other functions, particularly in leg prostheses, such as damping the shock which occurs when the prosthesis is set down and enabling a rotating movement of the foot relative to the stump.

Particularly in the designing of leg prostheses due account must be taken of the stability of the prosthesis. On the one hand an artificial knee must be able to carry out its pivoting function while an the other hand substantially no unintended bending may occur during the standing or straightened position. Stability is generally achieved by knee joints which make use of kinematic multiple rod systems, wherein at least four rods are applied. Such four-rod mechanisms are however relatively large and therefore less acceptable cosmetically. Another drawback is that the length of the lower leg in the sitting or bent and the standing or straightened position is generally not the same. This is perceived as very unpleasant by the patient.

Aspects relating to comfort are particularly associated with the means for fixing the prosthesis to the stump. The known leg prostheses comprise for instance an elongate tube of synthetic resin which is pushed over the stump. The drawback of such synthetic resin tubes however is that they produce transpiration and irritation. In addition, removal of the tube from the stump is not simple and unpleasant. Such tubes are particularly unsuitable for exarticulations because the patient here still has the thicker extremity of the bone. Tubes can really only be employed effectively in the case of a slightly tapering stump.

As already stated above, the part of the prosthesis replacing the amputated extremity also has to fulfill two important requirements. In the case of leg prostheses the shock occurring when the prosthesis is set down must be absorbed. In addition, a rotating of the foot relative to the stump can occur during movement of the body. During walking for instance the foot will be turned 10° inward and 10° outward, while during kneeling the rotation is even 45°. Means have already been proposed to absorb the torsional stress caused by this rotation. While such systems allow a rotation of between 10° and 20°, the occurring torsional stresses limit this angle to a few degrees. This is insufficient, particularly for kneeling.

The present invention has for its object to provide a prosthesis with which the problems occurring in the known prostheses or components thereof are obviated, and which is comfortable, cosmetically acceptable and easily manageable.

SUMMARY OF THE INVENTION

This is achieved by the invention with a prosthesis comprising two prosthesis parts connected for mutual movement and actuable means for locking respectively releasing the prosthesis parts relative to each other. The locking means provide sufficient stability, while the structural size of the prosthesis remains small so that no cosmetic problems occur. The prosthesis parts are preferably connected for mutual movement by means of an artificial joint which consists of a first joint part which forms part of or is coupled to the first prosthesis part and a second joint part which forms part of or is coupled to the second prosthesis part. Such an artificial joint is of course only necessary in cases where more than the lower leg has been amputated.

The locking means according to the invention preferably consist of a tiltable locking element under spring bias, a part of which co-acts in the locked position with a recess in one of the joint parts, whereby tilting of the locking element is bounded, and which in the released position is substantially freely tiltable. The recess in one of the two joint parts makes free tilting of the locking element impossible. Only when the locking element is placed outside the active reach of the limiting recess can the locking element tilt and release the joint.

This placing of the locking element outside the active reach of the limiting recess can take place in different ways. It is conceivable for instance to provide an element which presses the locking element as it were out of the active reach of the limiting recess, thus bringing about release. Such a system will be further designated as active release system.

This active release system can be applied in a joint which is embodied such that only active release is possible. In addition, embodiments of the invention can be envisaged wherein release takes place by means of body signals. Such embodiments can however also contain the active release system.

The first embodiment with only active release is of particular importance for patients who do not have enough muscle function available to operate the locking mechanism by means of body signals.

In the second embodiment of the invention release takes place passively by means of the walking movement. The artificial joint is formed for this purpose such that a pressure on the artificial joint caused by walking places the locking element out of the active reach of the limiting recess.

During walking one leg is raised while the other remains standing. A step can only taken when the leg that is lifted is bent. The bending for the following step already begins in the standing or straightened position. The foot of the standing or straightened leg shifts from heel to toe. The body weight is displaced forward. The release must be effected at the moment that the leg supports on the toe, since thereafter bending of the leg, i.e. a swinging of the lower leg, must be possible. In the second embodiment release is brought about by the forces which occur as the foot tips forward. Starting from a side view of the artificial joint the substantially right angle between the imaginary horizontal axis of one joint part and the imaginary vertical axis of the other joint part is slightly reduced. Due to this angle reduction the first prosthesis part enters into co-action with the locking element and thus causes a tilting thereof to the released position. The release of the joint is thus brought about. In this embodiment means are provided which enable an angle reduction. Such mean are omitted in the first embodiment.

During walking the lower leg is again brought at a particular moment into line with the upper leg, whereafter the leg is set down. The lower leg, which has remained behind at the location of the standing position while the upper leg moved forward with the rest of the body, is herein swung forward, back to the locked, standing or straightened position. For a smooth movement it is necessary that a swung-out lower leg returns quickly to its standing or straightened position. In order to realize this the prosthesis according to the invention comprises accelerating means, for instance elastic bands which are connected to both the first joint part and to the second joint part and which during bending of the joint are stretched to the maximum and then spring back, wherein the second joint part is carried along therewith.

When the lower leg is almost back in its standing or straightened position, the movement must preferably be braked to prevent the lower leg locking abruptly. To this end the prosthesis according to the invention provides braking means which are formed by brake elements in the one joint part co-acting with a run-off face in the other joint part. Such brake elements are for instance protrusions projecting slightly outside the joint part.

In order to prevent an unpleasant clicking sound during locking of the artificial joint the locking element is preferably provided with sound-damping means such as rubber protrusions on the contact surface between the locking element and the first joint part.

In preference the artificial joint is further provided with means for fixedly holding the locking element temporarily in the released position. This prevents the prosthesis snapping back into the locked position before a walking movement has been started. The locking element is preferably manufactured from a ferromagnetic material and the holding means are formed by a magnet. During the pivoting movement of the second joint part the contact surface between magnet and locking element becomes smaller until the locking element is released. Undesired locking is no longer possible at this moment because the locking element is situated outside the active reach of the recess.

When the prosthesis is a lower leg prosthesis for an exarticulations patient the invention makes it possible that the lower leg length in standing or straightened position is substantially the same as the lower leg length in sitting or bent position. This is achieved by the invention in that the axis of the hinge of the artificial joint is positioned at the height of the imaginary hollow of the knee or shifted over a line running at an angle of substantially 45° relative to the horizontal between the imaginary hollow of the knee and the imaginary centre of the broad extremity of the stump.

One of the two prosthesis parts connected for mutual movement is in any case formed by means for fixing the prosthesis to the remaining part of an amputated extremity. According to the invention a cup is preferably provided for receiving the extremity of the stump, means for fixing the prosthesis part to a higher located part of the stump and means for mutually connecting the cup and the fixing means. As already stated above, the known fixing means are formed by synthetic resin tubes which are sucked fast onto the stump by means of underpressure. It is thought that in the case of exarticulations it is not possible to make use of underpressure because around the knee and thus round the extremity of the stump fewer soft parts are present, whereby a vacuum can be sustained less well.

The cup according to the invention nevertheless makes use of vacuum. For this purpose the cup is provided on its open side with a sealing ring of flexible material with which the cup is hermetically sealed when the extremity of the stump is situated in the cup. The stump is then as it were sucked fast.

When the stump is placed in the cup the interior of the cup will have to be vented. A valve for instance can be provided for this purpose. The reverse is the case when the prosthesis is removed. Due to the underpressure inside the cup it is not possible to pull the stump out of the cup. Air can therefore be admitted to the interior of the cup via a valve whereby removal of the prosthesis is facilitated.

In a preferred embodiment of the invention the fixing part is provided, preferably close to its top part, with actuating means for the actively operated release mechanism. The patient can hereby effect the release in quite simple manner with a simple hand movement.

The second prosthesis part is a device for replacing at least a part of the amputated extremity. This replacement part has two other functions, however. In order to absorb the shock of setting down the foot the replacement part is provided with damping means. The damping means are preferably manufactured from a visco-elastic material such as polyurethane. Applied in the replacement part, polyurethane can be compressed a maximum of 10 mm. During normal walking only 6–7 mm compression is necessary. The (visco-)elastic material has an additional advantage, that is, it is very suitable for absorbing torsional stress. The rotating movement the foot makes relative to the stump exerts a torsional stress thereon. Unless this stress is well absorbed this is very unpleasant for the patient. The very (visco-) elastic material such as polyurethane used as damper in the device according to the invention can rotate 180°. Such a large rotation will not be necessary very often in practice.

The (visco-)elastic behaviour of the damping means is used as follows. A rotator in a leg prosthesis must enable an angular rotation of the prosthesis foot relative to the stump. This angular rotation must occur when turning moments are acting on the prosthesis leg. After the turning moments have disappeared, the foot must return again to the original position relative to the prosthesis leg. When the foot springs back the elasticity must be damped rapidly. It is undesirable to allow the foot to undergo multiple oscillations before the neutral position is used. For this purpose a damping element is generally added to the system. In the rotator of the invention this damping now stems from the use of (visco-) elastic material. This material has damping properties in addition to elastic properties. The use of a (visco-) elastic material with good damping properties, for instance (but not necessarily) polyurethane, enables integration of the elasticity and damping in one element.

The replacement part according to the invention consists substantially of two tubes mutually connected with interposing of a slide bearing, wherein in each of the tubes is received an outer end of a damping element simultaneously serving as torsional stress absorbing meals.

The replacement part, also known as rotator, is characterized by a self-adjusting stiffness. This operates in the following way. During a walking cycle high bending moments occur particularly at the beginning of the standing phase and at the end of the standing phase. In the case of a leg prosthesis user these moments must be transmitted through the replacement part (or rotator). This means that high bending moments also act on the means for absorbing torsional stress placed in this replacement part. These moments result in an increase in the normal forces in the bearing. The fact that there is a slide bearing in the rotator of the invention results in a greater increase in the friction than would be the case with ball bearings. This friction influences the torsional stiffness. The result is therefore that both at the beginning and the end of the standing phase there is a higher torsional stiffness. This is agreeable for the wearer of the prosthesis because stronger torsion of the foot relative to the prosthesis tube is undesirable during these phases.

The self-adjusting effect therefore depends on moment. Moments occurring during walking are substantially dependent on the weight of the walker. In the case of a heavy prosthesis wearer higher moments will occur than in the case of a light prosthesis wearer. This applies to both bending moments and torsional moments. Normalized to the walker's own weight the variation in moments between persons is however less great. If a rotator in a leg prosthesis now has a constant, i.e. not weight-dependent, torsional stiffness, this means that the angular rotation for heavier prosthesis users is greater than for lighter ones. This is undesirable. Because the torsional stiffness of the rotator of the invention increases as the bending moments on the rotator increase, the resulting torsional stiffness will be higher for heavy prosthesis users than for light prosthesis users. The occurring turning moments are however also greater for heavier prosthesis users. The effect is that the angles resulting during walking will hardly vary with the weight of the prosthesis user.

In the ideal case a prosthesis according to the invention will consist of three separate components, fixing part, artificial joint, replacement part. Shorter prostheses wherein no artificial joint is required will however consist only of the fixing part and the replacement part. It will of course be apparent to a skilled person that each of these three components can also be used in combination with conventional components. It is thus possible for instance to use the artificial joint in combination with the conventional cup and a conventional replacement part. All other conceivable combinations of the three components according to the invention with known components also fall within the scope of the present invention.

BRIEF DESCRIPTION OF THE DRAWINGS

The present invention will be further elucidated on the basis of the annexed drawings wherein corresponding reference numerals refer to corresponding components, and wherein.

DESCRIPTION OF THE PREFERRED EMBODIMENTS

Figure 1:
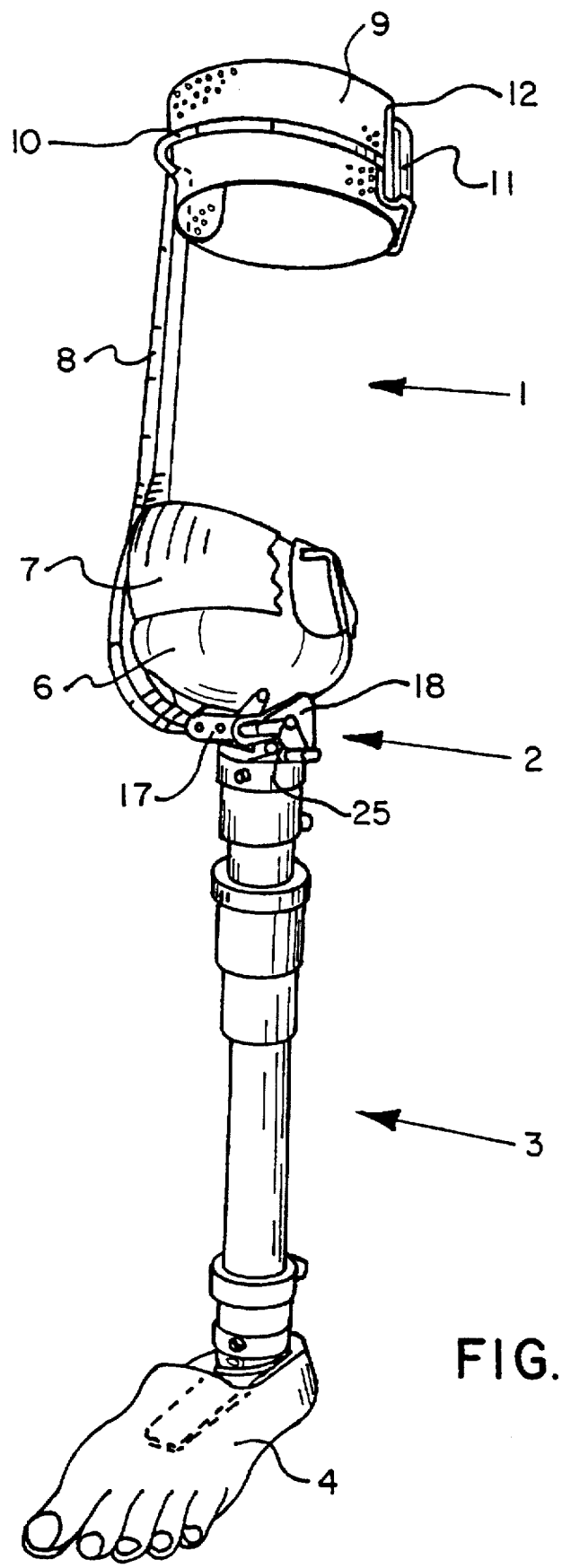
FIG. 1 shows a partly broken away perspective view of a prosthesis according to the invention.

FIG. 1 is an outline drawing of an embodiment of a prosthesis according to the invention. The prosthesis is constructed from a fixing part 1, an artificial joint 2, a replacement part 3 and an artificial toot 4 which forms part of the replacement part. The fixing part is built up of a cup 6 which is provided with a sealing ring 7 for sealing the cup from the outside environment, whereby a vacuum built up in the cup is sustained when the stump is situated in the cup. The cup is connected via a rod 8 to higher positioned fixing means which consist of a brace 10 in which a perforated band 9 is received. By means of for instance velcro tape 11 passed through an eye 12 the size of the fixing means can be adapted.

Figure 2:
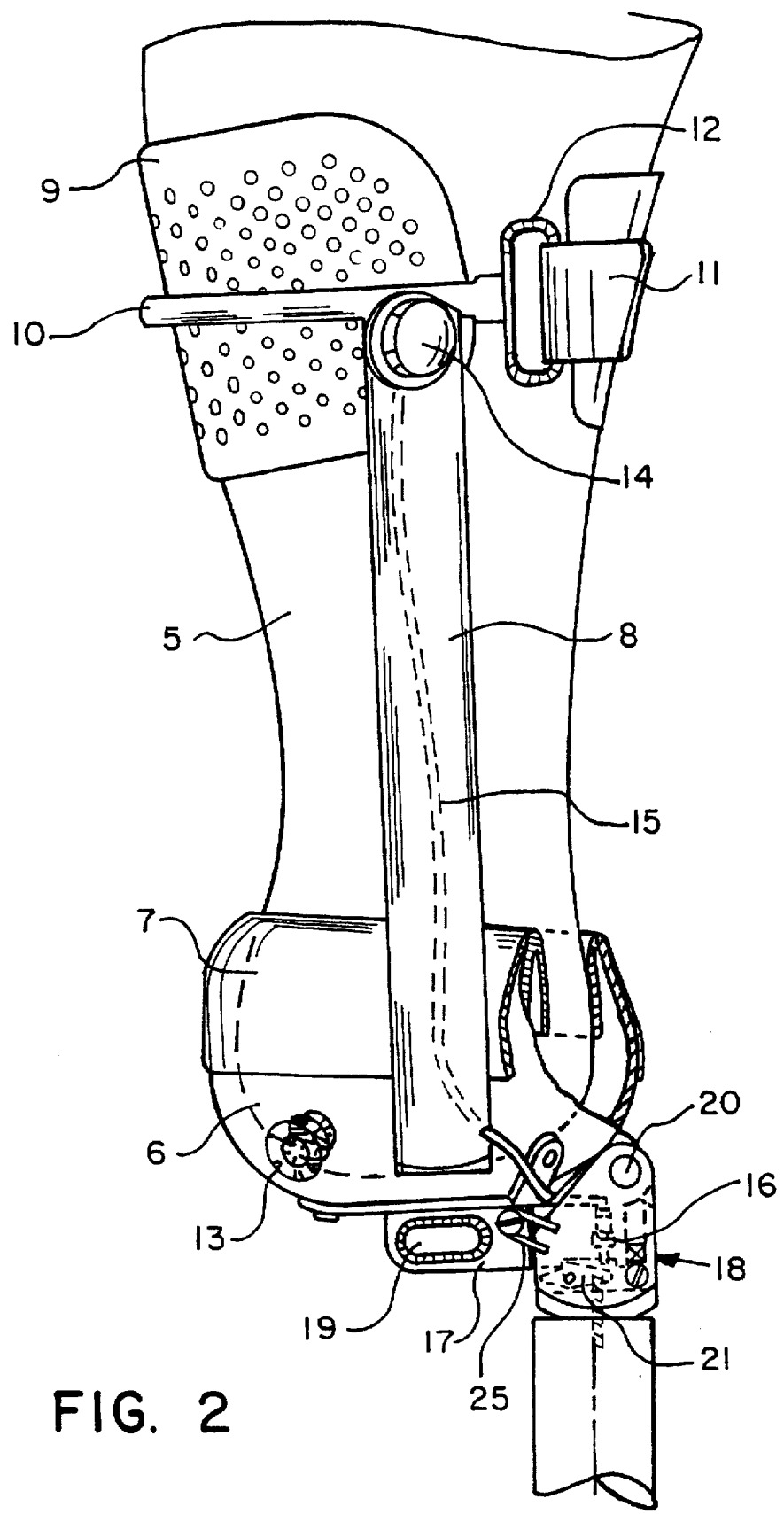
FIG. 2 shows a partly broken away detail view of the fixing part of a prosthesis according to the invention.

FIG. 2 shows a partly broken away side view of the fixing part with the stump 5 received therein. It can be seen here that cup 6 is provided with a valve 13. When stump 5 is placed into the cup venting can take place via this valve. An underpressure is thus created inside the cup whereby this latter is as it were sucked fast onto the stump. When the prosthesis is removed air can be admitted into the cup via the valve, whereby the suction action of the underpressure built up therein is discontinued and the stump can easily be taken out of the cup.

Transpiration is substantially prevented by the open structure of the fixing part. Irritation, which can occur particularly in the case of a closed tube, is also avoided.

Situated in this embodiment of the invention on the top part of rod 8 is a push-button 14 which is connected to a hose 15. By pressing push-button 14 the pin 16 is actuated whereby the locking element 21 of the artificial joint is carried outside the active reach of the recess in the first joint part 17, whereby release takes place.

The rod 8 is received in an opening 19 in the first joint part 17 of the artificial joint.

Figure 3A:
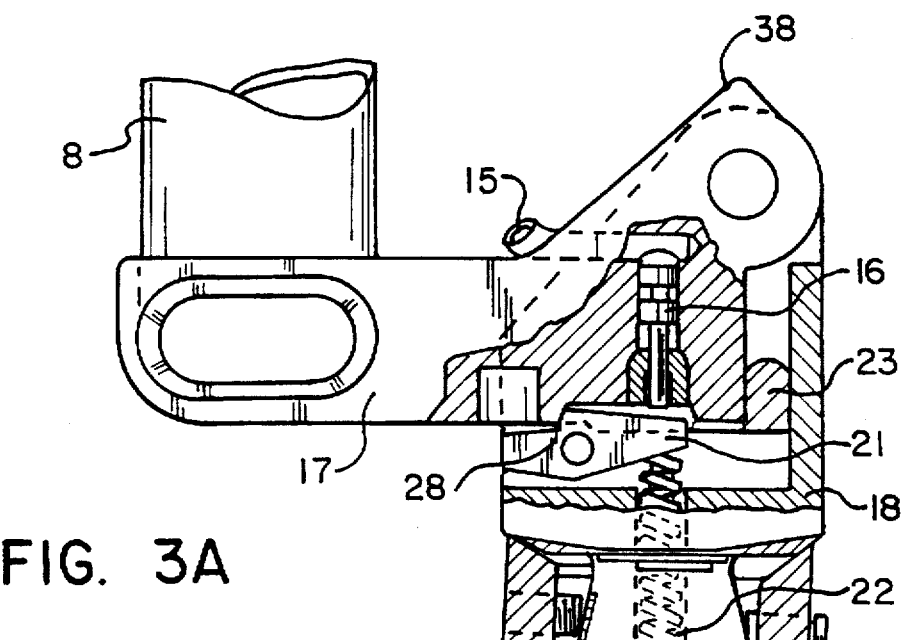
FIG. 3A shows a partly broken away side view of an artificial joint according to the invention in the locked situation.
Figure 3B:
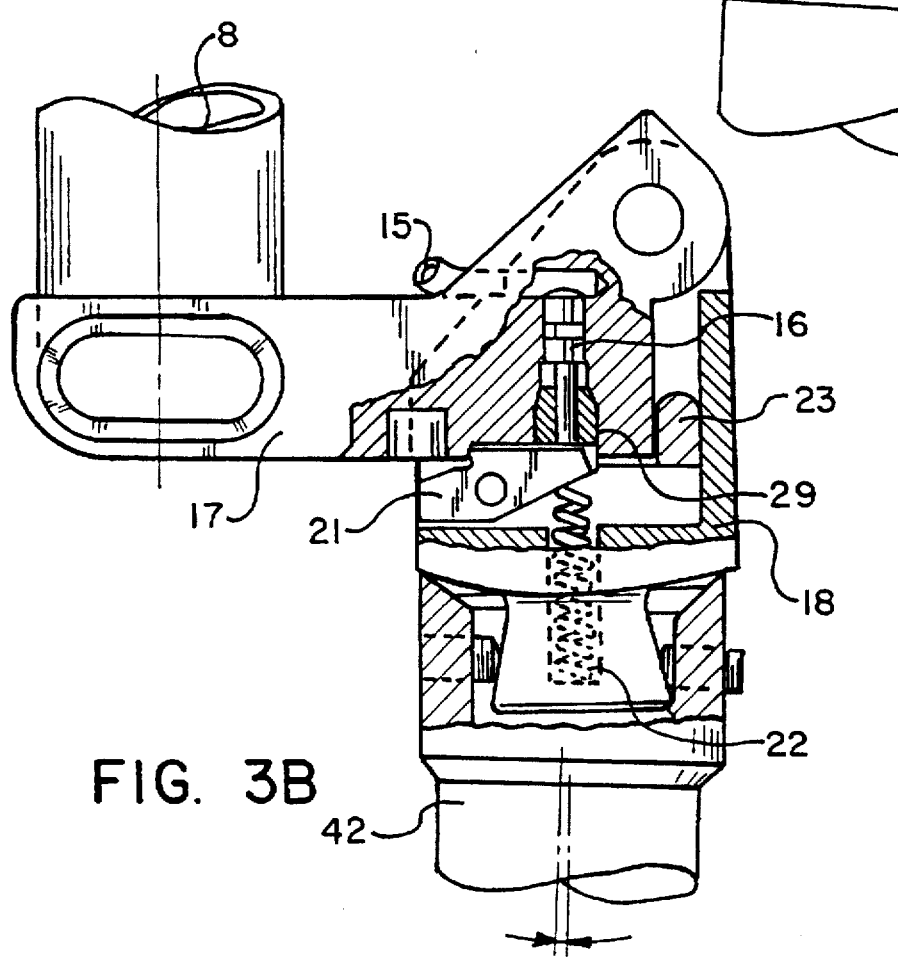
FIG. 3B shows a partly broken away side view of an artificial joint according to the invention in a position displaced slightly relative to that shown in FIG. 3A but still locked.
Figure 4:
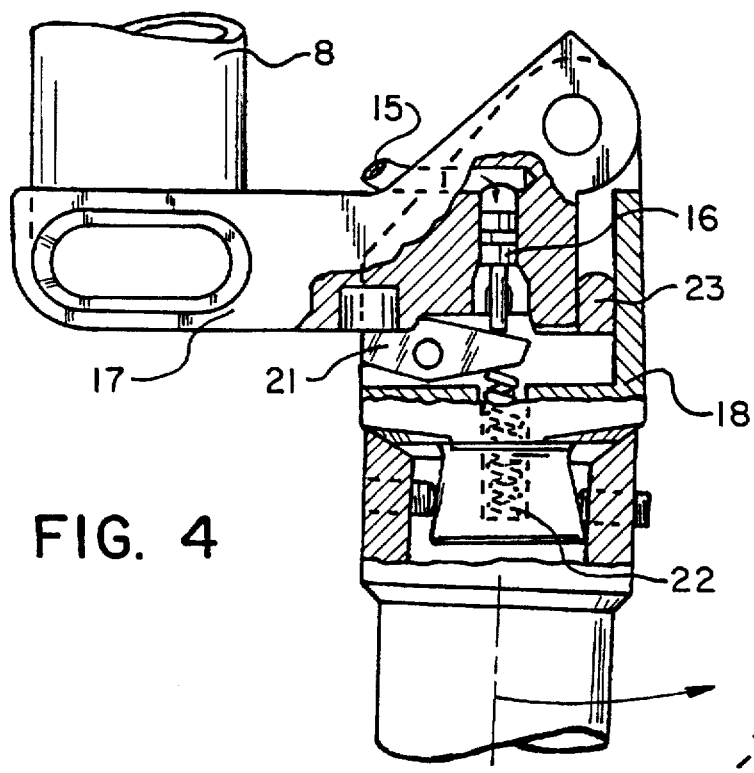
FIG. 4 shows the release of the artificial joint of FIG. 3 by means of a pneumatically actuated pin.

FIGS. 3A to 5 show one embodiment of the artificial joint according to the invention with an active release system. The joint is constructed from a first joint part 17 and a second joint part 18. The first joint part 17 is coupled via a rod 8 to the fixing part, the second joint part is received in the replacement part. Received in the second joint part 18 is a locking element 21 which falls partially within the active reach of a recess 27 of the first joint part 17. In the situation shown in FIG. 3A the locking element 21 strikes against a first contact surface 28. The first joint part 17 itself strikes against a blocking element 23 of rigid material. In the blocked position of this embodiment the two joint parts can pivot slightly in relation to each other between two end positions. The first end position is shown in FIG. 3A wherein the locking element 21 strikes against the first contact surface 28. The second end position is shown in FIG. 3B. Here the locking element 21 strikes against the contact surface 29. In this situation the first joint part makes no contact with the blocking element 23. Due to the co-action of the recess and the locking element pivoting of joint part 18 relative to joint part 17 is prevented. In this embodiment release can only take place by pneumatic operation of the pin 16 via hose 15. The pin carries locking element 21, counter to the action of spring 22, outside the active reach of recess 27. This results in release. The second joint part 18 together with the replacement part connected thereto is now able to swing outward in the direction of the arrow shown in FIG. 4.

Figure 5:
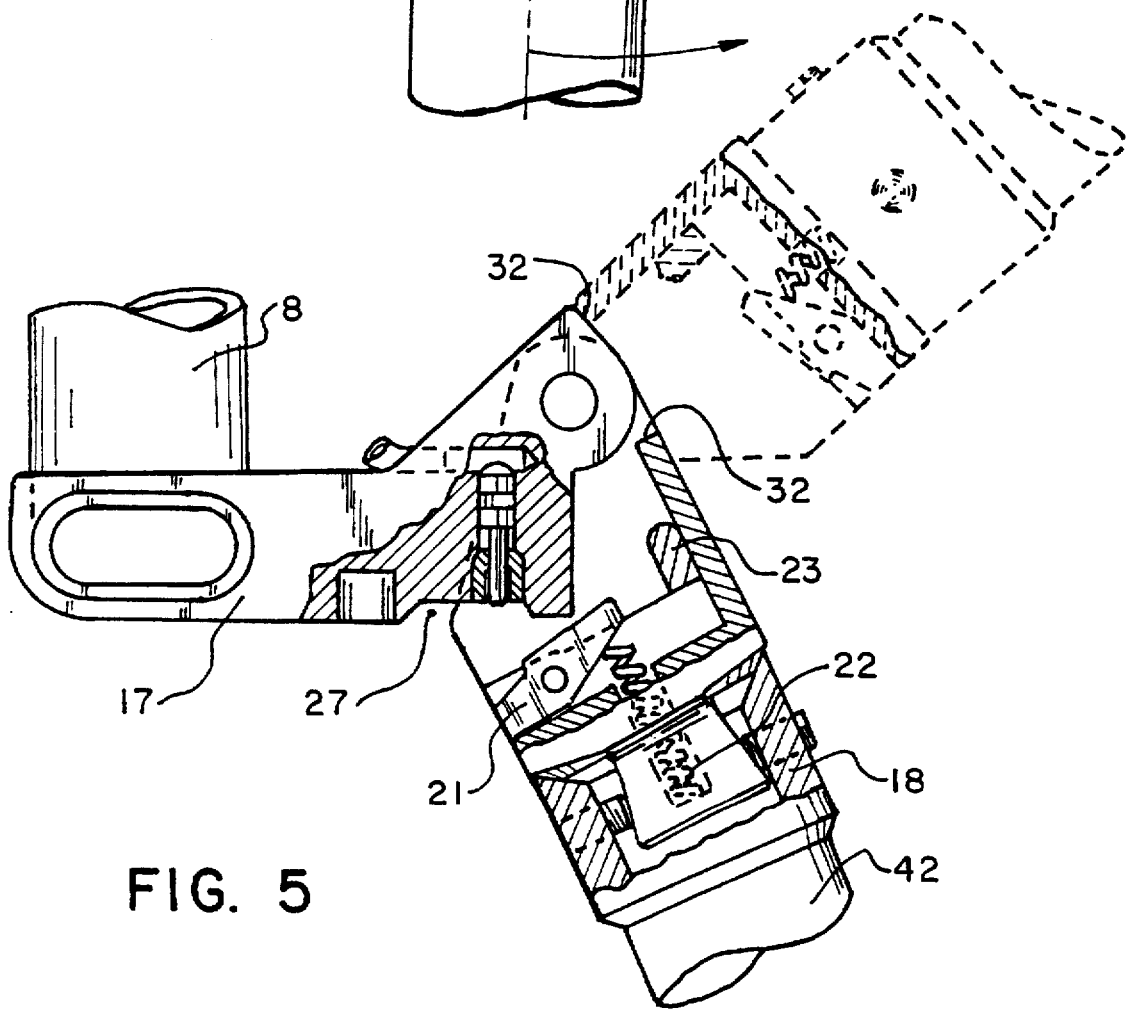
FIG. 5 shows a partly broken away side view of the released artificial joint of FIG. 3 in a random position and an extreme position.

FIG. 5 shows the outermost position of the second joint part 18 relative to the first joint part 17. Such a position occurs for instance in the case of kneeling. The second joint part 18 is provided with a limiting element 32 which in the outermost position strikes against the stop 38 on the first joint part 17. In this situation the elastic bands are already beyond their maximum stretched state.

Figure 6:
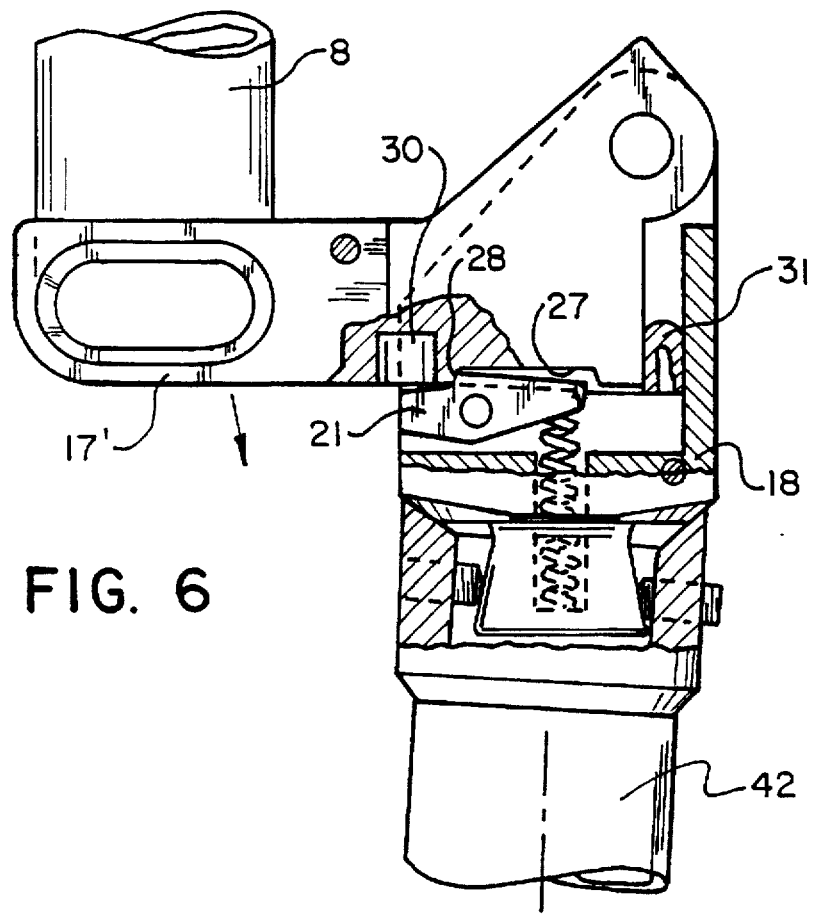
FIG. 6 shows a partly broken away perspective side view of a second embodiment of the artificial joint according to the invention in locked situation.
Figure 7:
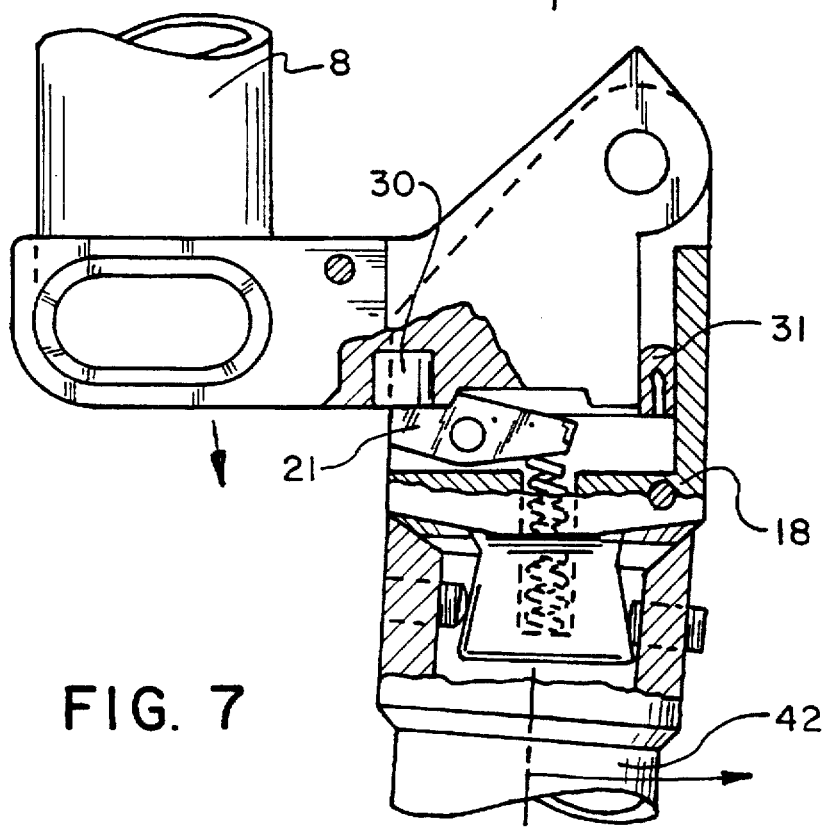
FIG. 7 shows a partly broken away side view of the second embodiment of the artificial joint according to the invention in released situation.

A second embodiment of the invention is shown in FIGS. 6 and 7. The rigid blocking element 23 is replaced in this embodiment by a spring 31. This makes it possible to slightly reduce the substantially right angle between the vertical axis of the second joint part and the horizontal axis of the first joint part. The first joint part 17' then brings about a tilting of the locking element 21 through contact via the first contact surface 28 with the locking element. The locking element is hereby placed outside, the reach of the recess 27 and release can take place.

In FIG. 7 is shown how the locking element 21 is held in the released position by a magnet 30. During pivoting of both joint parts relative to each other locking element 21 slides along the magnet 30 until it moves outside the active reach of the magnet and, under the influence of the spring action of spring 22, tilts back into its starting position. Release has then already been effected however, and the second joint part with the replacement part can move relative to the first joint part.

Figure 8:
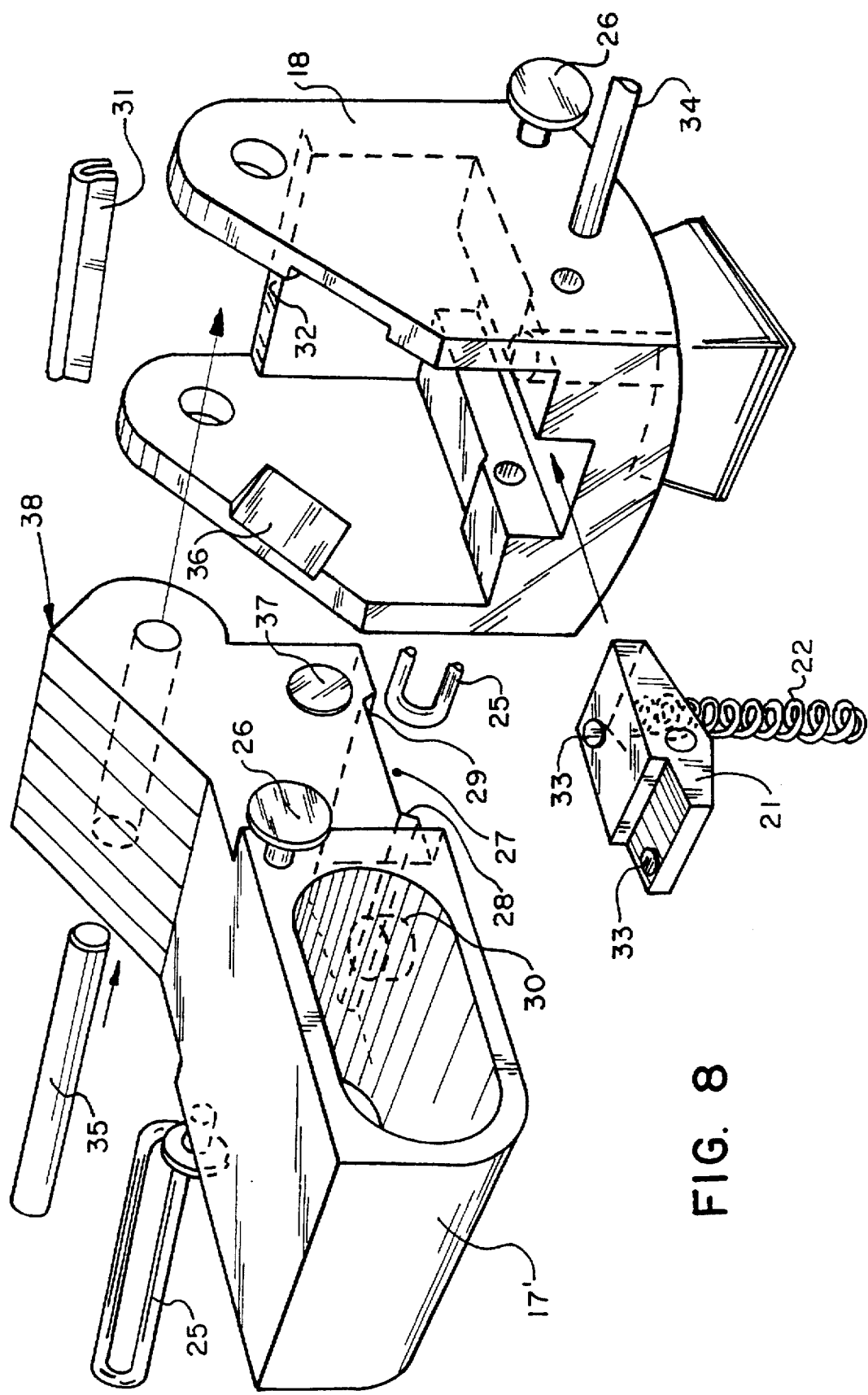
FIG. 8 is a perspective view with exploded parts of an artificial joint according to the invention.

FIG. 8 shows the artificial joint according to the invention with exploded parts. The first joint part 17' can be seen with the recess 27 arranged therein. The joint part 17' is provided with a magnet 30 for holding locking element 21 fixedly in the released situation for a short time. Knobs 26 are situated on the sides of the joint part 17'. Similar knobs are likewise situated on joint part 18. Elastic bands 25 are arranged between both knobs. These elastic bands ensure that at the end of its movement the swung-out prosthesis part returns quickly to the standing or straightened position of the prosthesis. The locking element 21 is provided with sound-damping blocks 33, for instance of rubber. Blocks 33 provide a sound-damping when the locking element tilts from the one position to the other. The first joint part 17' is further provided with slightly protruding brake elements 37 which co-act with run-off surfaces 36 in joint part 18. At the end of the movement to the standing or straightened position of the prosthesis this movement is braked by means of the brake elements 37 and run-off surfaces 36. This prevents abrupt locking of the artificial joint. Further shown in FIG. 8 is the spring 31 as this is applied in the second embodiment of the invention. Also shown are shafts 34 and 35 for arranging in the second joint part 18 respectively the locking element 21 and the first joint part 17'. The drawing further shows the limiting element 32 which in the assembled situation co-acts with the stop 38.

Figure 9:
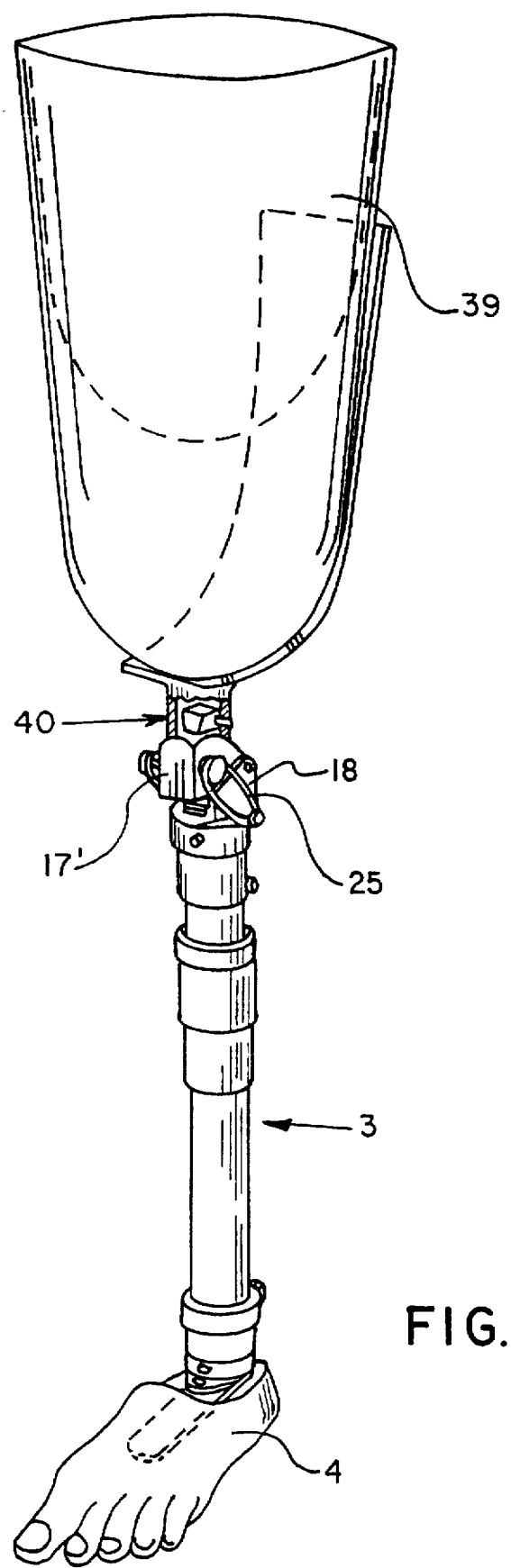
FIG. 9 shows a combination of conventional cup with the artificial joint and the replacement part according to the invention.

FIG. 9 shows a situation wherein the replacement part according to the invention and the artificial joint are applied together in combination with a conventional cup. The first joint part 17' has for this purpose a slightly adapted top part 40.

Figure 10:
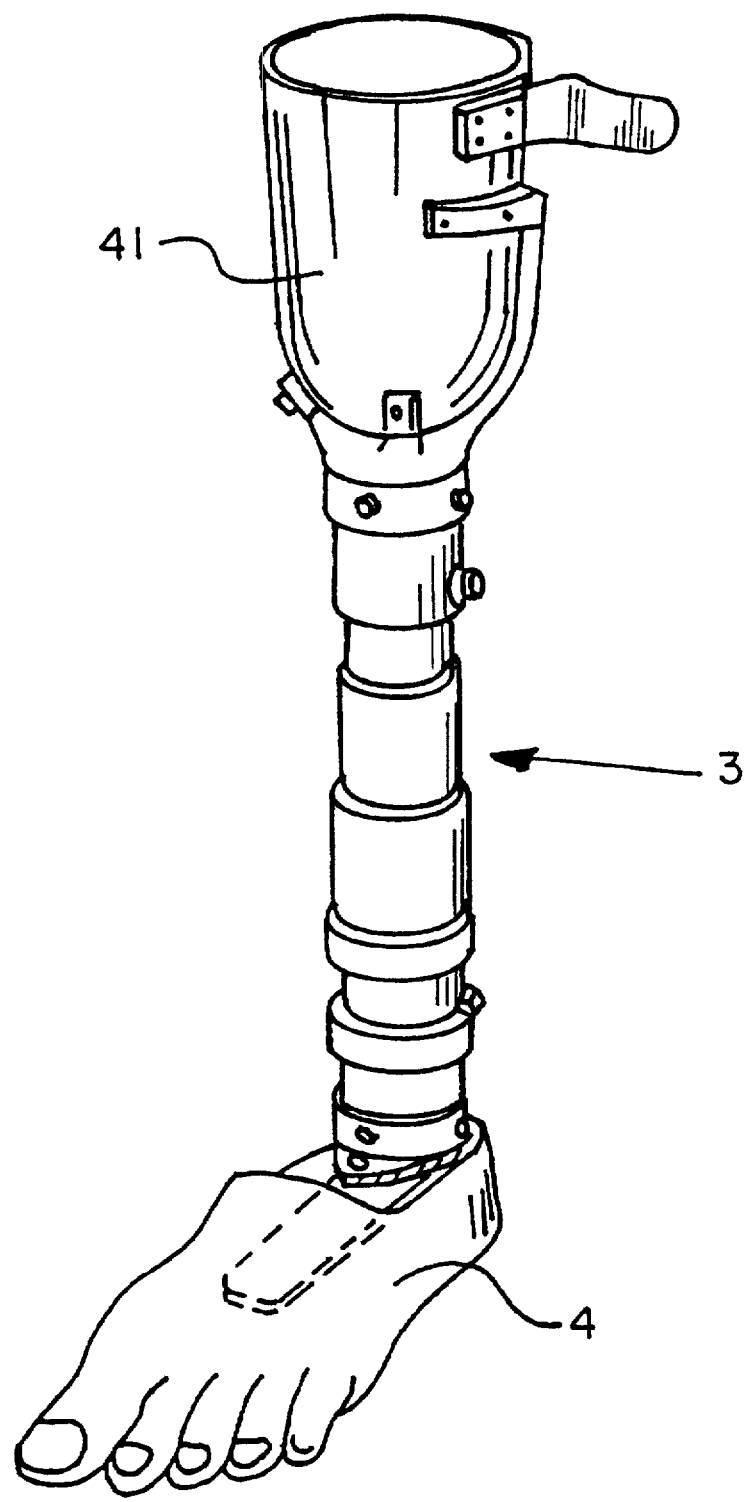
FIG. 10 shows a lower leg prosthesis wherein the artificial joint is omitted.

FIG. 10 shows that it is likewise possible to employ only the replacement part with a conventional cup without interposing of the artificial joint. This relates to a lower leg prosthesis wherein the knee joint still exists. Such a prosthesis nevertheless also has all advantages relating to shock-damping and torsional stress absorption of the replacement part according to the invention.

Figure 11:
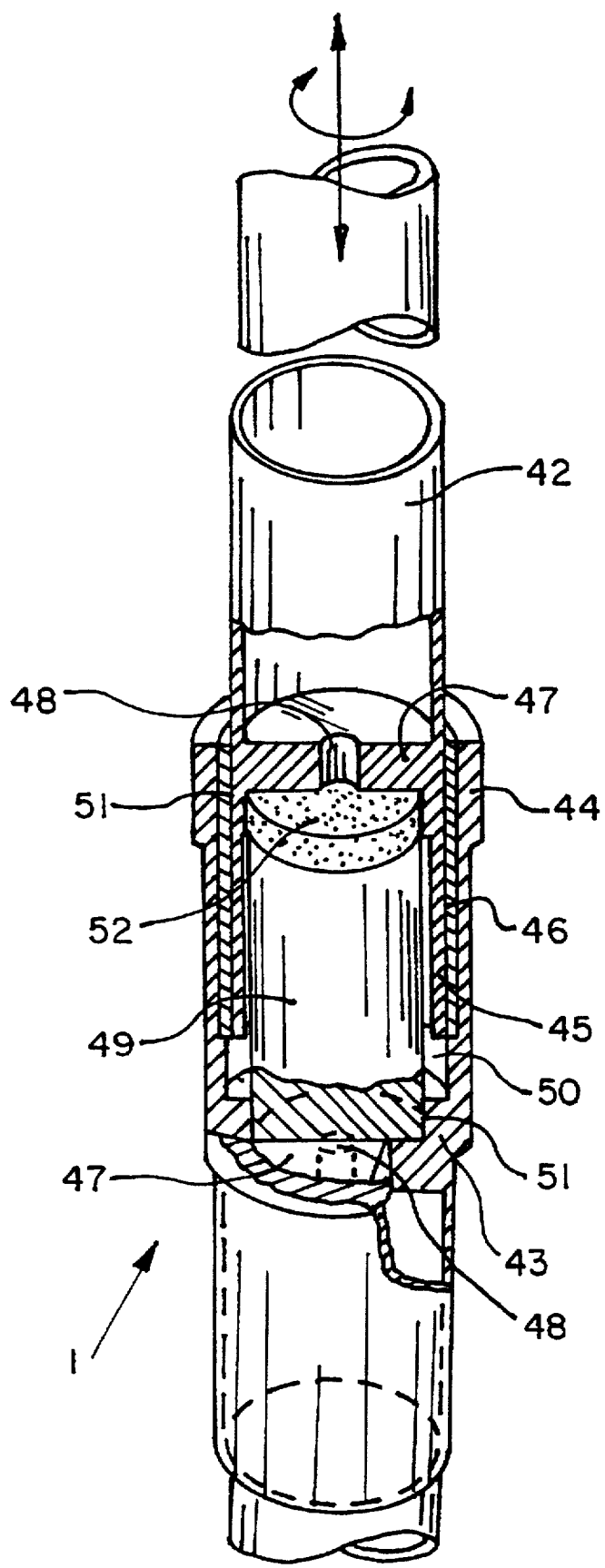
FIG. 11 is a partly broken away perspective view of the damping rotating element of the replacement part according to the invention.

FIG. 11 finally shows a partly cut away perspective view of the replacement part 3 according to the invention. The part 3 is constructed from two tubes 42 and 43, and the outer end of tube 43 is formed such that it provides a sleeve 44 in which is received the outer end 45 of tube 42. Between outer end 45 and sleeve 44 is situated a slide bearing 46. This latter enables a smooth rotation of both parts relative to each other. Arranged in both tubes are transverse partitions 47 which are provided with apertures 48. Situated between the transverse partitions is a damper 49 of a (visco-)elastic material, preferably polyurethane, which is fixed by means of glue 52 in both tubes 42 and 43 at the height of a shoulder 51. Apertures 48 enable venting of the damper during assembly. An air buffer 50 is likewise situated around the damper 49.

The present invention provides a fixing part which can be worn comfortably. In addition the invention provides an artificial joint which due to its small dimensions is cosmetically acceptable but still provides sufficient stability in the standing or straightened position. In accordance with the wishes of the patient the locking mechanism of the joint can be actuated actively or passively. There are even patients who can manage without locking mechanism but who still gain advantage from the small dimensions of the joint or the advantages of the other components. The invention finally provides a replacement device which enables good absorption of shocks and rotation load. The three components according to the invention can be used separately as well as in any conceivable combination and therefore fall within the scope of this invention either separately or in any combination.

We claim:

1. A prosthesis for replacing an amputated portion of a leg of a patient, the prosthesis comprising:
    a fixing part configured to receive a remaining part of the leg of the patient;
    a foot; and
    a torsion absorber connected between the fixing part and the foot for absorbing torsion stresses produced therebetween, the torsion absorber including:
        a first tube having a first end and a second end, with the first end of the first tube coupled to one of the fixing part and the foot;
        a second tube having a first end and a second end, with the first end of the second tube coupled to the other of the fixing part and the foot, with the second end of the second tube received in the second end of the first tube; and
        a slide bearing received between and in contact with the first tube and the second tube, with the slide bearing positioned between the second end of the first tube and the second end of the second tube, wherein at a beginning and an end of a stance phase of a walking cycle, the slide bearing, the first tube and the second tube coact to increase a torsion resistance between (i) the slide bearing and the first tube and (ii) the slide bearing and the second tube.

2. The prosthesis as set forth in claim 1, wherein the torsion absorber further includes a damper positioned inside the first tube and the second tube, with the damper coupled to the first tube and the second tube, wherein:
    the damper resists compression between the first tube and the second tube; and the damper resists torsion between the first tube and the second tube.

3. The prosthesis as set forth in claim 2, wherein:

the first tube and the second tube each include a transverse partition positioned therein between the ends thereof; and the damper has a first end secured to one of the transverse partitions and has a second end secured to the other of the transverse partitions.

4. The prosthesis as set forth in claim 3, wherein each transverse partition includes an aperture which extends between a side thereof coupled to the damper and a side thereof opposite the damper.

5. The prosthesis as set forth in claim 3, wherein:

the damper has a damper body which extends between the first end and the second end of the damper;

the first tube and the second tube each include a shoulder around the damper body adjacent the transverse partition thereof; and the shoulders, the damper, the first tube and the second tube define an air space around the damper body between the shoulders.

6. The prosthesis as set forth in claim 3, wherein the ends of the damper are coupled to the transverse partitions via glue.

7. The prosthesis as set forth in claim 3, further including:

a first prosthesis part having a first end and a second end, with the first end of the first prosthesis part coupled to the fixing part;

a second prosthesis part having a first end and a second end, with the first end of the second prosthesis part coupled to the torsion absorber; and an artificial joint connected between the second end of the first prosthesis part and the second end of the second prosthesis part, wherein the artificial joint includes:

a first joint part positioned at the second end of the first prosthesis part;

a second joint part positioned at the second end of the second prosthesis part, with a sagittal axis of the first joint part and a longitudinal axis of the second joint part forming a substantially right angle when the first prosthesis part and the second prosthesis part are aligned;

a hinge pivotally connecting the first joint part and the second joint part;

a locking mechanism positioned between the first joint part and the second joint part for locking the first joint part and the second joint part in alignment; and a release mechanism positioned adjacent the locking mechanism, wherein at the beginning stance phase of the walking cycle the substantially right angle reduces thereby causing the release mechanism and the locking mechanism to press together whereby the locking mechanism is released so that the first prosthesis part and the second prosthesis part can pivot with respect to each other around the hinge.

8. The prosthesis as set forth in claim 7, wherein when the first prosthesis part and the second prosthesis part are aligned, the hinge is positioned at a height shifted over a line running at an angle of substantially 45° relative to a horizontal between an imaginary hollow of the knee and a center of a broad outer end of the remaining part of the leg such that the second prosthesis part, in straightened and bent position, occupies the position of the amputated portion of the leg.

9. The prosthesis as set forth in claim 3, further including:

a first prosthesis part having a first end and a second end, with the first end of the first prosthesis part coupled to the fixing part;

a second prosthesis part having a first end and a second end, with the first end of the second prosthesis part coupled to the torsion absorber; and an artificial joint connected between the second end of the first prosthesis part and the second end of the second prosthesis part, wherein the artificial joint includes:

a first joint part positioned at the second end of the first prosthesis part;

a second joint part positioned at the second end of the second prosthesis part; and a hinge pivotally connecting the first joint part and the second joint part, wherein when the first prosthesis part and the second prosthesis part are aligned, the hinge is positioned at a height shifted over a line running at an angle of substantially 45° relative to a horizontal between an imaginary hollow of the knee and a center of a broad outer end of the remaining part of the leg such that the second prosthesis part, in straightened and bent position, occupies the position of the amputated portion of the leg.

10. The prosthesis as set forth in claim 9, wherein the artificial joint further includes:

a locking mechanism positioned between the first joint part and the second joint part for locking the first joint part and the second joint part in alignment; and a release mechanism positioned adjacent the locking mechanism, wherein:

when the first joint part and the second joint part are aligned, a sagittal axis of the first joint part and a longitudinal axis of the second joint part form a substantially right angle; and at the beginning stance phase of the walking cycle the substantially right angle reduces thereby causing the release mechanism and the locking mechanism to press together whereby the locking mechanism is released so that the first prosthesis part and the second prosthesis part can pivot with respect to each other around the hinge.

11. The prosthesis as set forth in claim 2, wherein the damper is formed from visco-elastic material.

12. The prosthesis as set forth in claim 11, wherein the visco-elastic material is polyurethane.

13. A torsion absorber coupled to a prosthesis part connected between an artificial foot and a fixing part, with the fixing part configured to receive a remaining part of an amputated leg of a patient, with the torsion absorber configured to absorb torsion stresses produced between the fixing part and the foot, the torsion absorber comprising:

a first tube having a first end and a second end, with the first end of the first tube coupled to one of a foot and a fixing part;

a cylindrical slide bearing received in the second end of the first tube so that an exterior surface of the cylindrical slide bearing is in contact with an interior surface of the first tube; and a second tube having a first end and a second end, with the first end of the second tube coupled to other of the foot and the fixing part, with the second end of the second tube received in the cylindrical slide bearing so that an exterior surface of the second tube is in contact with an interior surface of the cylindrical slide bearing, wherein:

the cylindrical slide bearing, the first tube and the second tube coact so that bending moments of the prosthesis increase normal forces in the cylindrical slide bearing; and the increase in the normal forces increases a torsion resistance between (i) the slide bearing and the first tube and (ii) the slide bearing and the second tube.

14. The torsion absorber as set forth in claim 13, further including an elastic damper positioned inside the first tube and the second tube, with the damper coupled to the first tube and the second tube whereby the damper resists compression and torsion between the first tube and the second tube.

15. The torsion absorber as set forth in claim 13, wherein intermediate a beginning and an end of a stance phase of a walking cycle the normal forces in the slide bearing have values less than the normal forces in the slide bearing at the beginning and the end of the stance phase of the walking cycle.

* * * * *

UNITED STATES PATENT AND TRADEMARK OFFICE
CERTIFICATE OF CORRECTION

PATENT NO. : 5,895,429
DATED : April 20, 1999
INVENTOR(S) : Jan Constant Cool et al.

It is certified that error appears in the above-identified patent and that said Letters Patent is hereby corrected as shown below:

Column 1 after Line 3 insert: --1) Field of the Invention--., delete --FIELD of THE INVENTION--.

Column 1 after Line 7 insert: --2) Background Art--.

Column 1 Line 30 "an the other hand" should read --on the other hand--.

Column 2 Lines 64-65 "Such mean" should read --Such means--.

Column 3 Line 39 "exarticulations" should read --exarticulation--.

Column 4 Line 52 "meals." should read --means.--.

Column 6 Line 15 "toot 4" should read --foot 4--.

Column 7 Line 23 after "outside" delete comma --,--.

Signed and Sealed this

Twenty-third Day of May, 2000

Attest:

Attesting Officer

Q. TODD DICKINSON

Director of Patents and Trademarks